(12) United States Patent
Goto et al.

(10) Patent No.: US 8,862,207 B2
(45) Date of Patent: *Oct. 14, 2014

(54) FLUOROSCOPIC IMAGING SYSTEM

(75) Inventors: Masashi Goto, Kanagawa (JP); Shigeru Nemoto, Tokyo (JP)

(73) Assignees: Resource One Inc, Kanagawa (JP); Nemoto Kyorindo Co., Ltd., Tokyo (JP)

( * ) Notice: Subject to any disclaimer, the term of this patent is extended or adjusted under 35 U.S.C. 154(b) by 1694 days.

This patent is subject to a terminal disclaimer.

(21) Appl. No.: 12/295,768

(22) PCT Filed: Apr. 2, 2007

(86) PCT No.: PCT/JP2007/000355
§ 371 (c)(1),
(2), (4) Date: Oct. 2, 2008

(87) PCT Pub. No.: WO2007/125639
PCT Pub. Date: Nov. 8, 2007

(65) Prior Publication Data
US 2010/0160776 A1 Jun. 24, 2010

(30) Foreign Application Priority Data
Apr. 5, 2006 (JP) .................. 2006-104358

(51) Int. Cl.
A61B 6/00 (2006.01)
G06Q 50/00 (2012.01)
A61M 5/145 (2006.01)
G06F 19/00 (2011.01)
A61M 5/00 (2006.01)

(52) U.S. Cl.
CPC ........ *G06Q 50/00* (2013.01); *A61M 2205/3561* (2013.01); *A61B 6/504* (2013.01); *A61M 5/14546* (2013.01); *A61B 6/481* (2013.01); *G06F 19/321* (2013.01); *A61M 2205/3584* (2013.01); *A61M 5/1456* (2013.01); *A61M 2205/52* (2013.01); *A61M 5/007* (2013.01); *A61M 2205/3553* (2013.01); *G06F 19/3481* (2013.01)
USPC ........... 600/476; 600/407; 600/431; 600/432; 378/116; 378/98.2; 378/98.5

(58) Field of Classification Search
USPC ........... 600/407, 431, 432, 476; 378/11, 98.2, 378/98.56
See application file for complete search history.

(56) References Cited

U.S. PATENT DOCUMENTS 5,440,607 A * 8/1995 Nakaya .................. 378/98.2
7,379,655 B1 * 5/2008 Koyabu et al. .............. 386/296
(Continued)

FOREIGN PATENT DOCUMENTS

JP 2001-101320 4/2001
JP 2004-298550 10/2004
(Continued)

OTHER PUBLICATIONS

International Search Report for PCT/JP2007/000355 dated Jul. 10, 2007.

*Primary Examiner* — Baisakhi Roy
(74) *Attorney, Agent, or Firm* — Rankin, Hill & Clark LLP

(57) ABSTRACT

A liquid injector (400) injects a medical liquid into a patient whose fluoroscopic image data is to be picked up and generates injection history data corresponding to the injection, and a control box (500) registers the injection history data in a RIS (100) in association with imaging order data. Accordingly, the RIS (100) also stores the injection history data associated with the imaging order data, and therefore the injection history data can also be confirmed based on the imaging order data.

47 Claims, 9 Drawing Sheets

(56) References Cited

U.S. PATENT DOCUMENTS

| | | | |
|---|---|---|---|
| 7,430,341 B2* | 9/2008 | Takeo | 382/294 |
| 2004/0064040 A1* | 4/2004 | Masuda et al. | 600/431 |
| 2004/0162484 A1* | 8/2004 | Nemoto | 600/420 |
| 2004/0199076 A1* | 10/2004 | Nemoto | 600/432 |
| 2006/0002633 A1* | 1/2006 | Takeo | 382/294 |
| 2006/0064321 A1 | 3/2006 | Sasano et al. | |
| 2006/0074294 A1* | 4/2006 | Williams et al. | 600/420 |
| 2006/0184122 A1* | 8/2006 | Nemoto | 604/154 |
| 2007/0225601 A1* | 9/2007 | Uber et al. | 600/431 |
| 2008/0045930 A1* | 2/2008 | Makin et al. | 604/890.1 |
| 2009/0163802 A1* | 6/2009 | Goto et al. | 600/432 |
| 2010/0160776 A1* | 6/2010 | Goto et al. | 600/431 |
| 2010/0174181 A1* | 7/2010 | Nemoto | 600/431 |

FOREIGN PATENT DOCUMENTS

| | | |
|---|---|---|
| JP | 2005-198808 | 7/2005 |
| JP | 2006-061278 | 3/2006 |
| WO | 2005/007220 | 1/2005 |

\* cited by examiner

FLUOROSCOPIC IMAGING SYSTEM

TECHNICAL FIELD

The present invention relates to a fluoroscopic imaging system that includes an imaging diagnostic apparatus, a liquid injector and an image viewer, employed for picking up fluoroscopic image data from a patient to whom a medical liquid is injected, and to display such image.

BACKGROUND ART

Fluoroscopic imaging equipments currently available for picking up a tomographic image, which is fluoroscopic image data of a patient, includes a Computed Tomography (CT) scanner, a Magnetic Resonance Imaging (MRI) equipment, a Positron Emission Tomography (PET) equipment, and an ultrasonic diagnostic equipment. Also, medical equipments that pick up a vascular image, which is another fluoroscopic image data of the patient, include a CT angiographic equipment, a Magnetic Resonance Angiographic (MRA) equipment, and so forth.

When one of such equipments is used, the patient often undergoes an injection of a medical liquid (or simply liquid as the case may be), also called a medical fluid, such as a contrast medium or physiological saline, and liquid injector that automatically execute the injection are currently in practical use. A popular liquid injector retains a liquid syringe loaded with the liquid, and a piston member is press-inserted into the cylinder member of the syringe to thereby inject the liquid into the patient's body.

Although the imaging diagnostic apparatus can work on a stand-alone basis, normally a fluoroscopic imaging system is constituted, including the imaging diagnostic apparatus as part thereof. Such fluoroscopic imaging system also includes an imaging management unit and a data storage unit, respectively connected to the imaging diagnostic apparatus.

The imaging management unit, generally called a Radiology Information System (hereinafter, RIS) or alike, serves to manage imaging order data used for picking up a fluoroscopic image data of the patient, in other words shooting a fluoroscopic image and thereby generating the fluoroscopic image data of the patient. The imaging order data include, for example, an imaging job identity (ID) which is exclusive identification data, identification data of the imaging diagnostic apparatus, identification data of the patient, date and time of the start and finish of the imaging. Meanwhile, the imaging order, also called an inspection order in actual medical sites.

The imaging order data is provided to the imaging diagnostic apparatus from the imaging management unit. The imaging diagnostic apparatus then picks up the fluoroscopic image data of the patient in correspondence with the imaging order data. The fluoroscopic image data is allocated with at least a part of the imaging order data in the imaging diagnostic apparatus, and output to the data storage unit.

The data storage unit, generally called a Picture Archive and Communication System (PACS) or alike, stores therein the fluoroscopic image data allocated with the imaging order data.

To the data storage unit, an image viewer, generally called a viewer, is connected. The image viewer reads out the fluoroscopic image data utilizing, for example, the imaging order data as the retrieval key, and displays that fluoroscopic image data.

It is to be noted that the imaging management unit is usually engaged in managing a plurality of imaging order data. Accordingly, one of the plurality of imaging order data managed by the imaging management unit has to be selectively provided to the imaging diagnostic apparatus. For this purpose, the imaging management unit is designed either as a push-type or as a pull-type.

The push-type imaging management unit selects one of the plurality of imaging order data under the management, for example through manual operation by the operator. The push-type imaging management unit transmits, upon receipt of a response request for the imaging order data from the imaging diagnostic apparatus, the selected one of the imaging order data, in response thereto.

To the pull-type imaging management unit, the imaging diagnostic apparatus transmits an order retrieval key with the response request for the imaging order data. The order retrieval key is composed of an imaging job ID for example, of the imaging order data.

Then the imaging management unit retrieves the imaging order data with the order retrieval key, and transmits the imaging order data thus retrieved as response to the imaging diagnostic apparatus. Upon receipt of the legitimate imaging order data, the imaging diagnostic apparatus picks up the fluoroscopic image data of the patient in correspondence with the imaging order data.

On the other hand, in the case where a plurality of imaging order data is retrieved and returned, the imaging diagnostic apparatus selects one of the plurality of imaging order data received, through manual operation by the operator for example.

In addition, once the imaging order data transmitted by the imaging management unit is fixed in the imaging diagnostic apparatus as above, such effect is notified to the imaging management unit. Accordingly, with the pull-type imaging management unit also, the imaging order data used for picking up the fluoroscopic image by the imaging diagnostic apparatus can be identified.

Regarding the foregoing fluoroscopic imaging system, various proposals have been made (for example, patent documents 1 and 2).

[Patent document 1] JP-A No. 2001-101320
[Patent document 2] JP-A No. 2005-198808

DISCLOSURE OF THE INVENTION

Problem to be Solved by the Invention

In the foregoing fluoroscopic imaging system, the imaging diagnostic apparatus picks up the fluoroscopic image data of the patient, in other words shoots a fluoroscopic image thereby generating the fluoroscopic image data of the patient, in correspondence with the imaging order data, and the fluoroscopic image data is stored together with the imaging order data allocated thereto.

This makes it possible to retrieve the fluoroscopic image data with the imaging order data. Also, the imaging order data can be utilized for confirming the imaging condition and the like, when viewing the fluoroscopic image data.

However, despite that the patient who is to undergo the fluoroscopic image data pickup normally undergoes the injection of a medical liquid (hereinafter simply liquid as the case maybe), also called a medical fluid, such as a contrast medium as already stated, the injection condition is not included in the imaging order data. Accordingly, it is impossible to confirm how the liquid was injected into the patient when the fluoroscopic image data of that patient was picked up.

The present invention has been accomplished in view of the foregoing problem, with an object to provide a fluoroscopic imaging system that enables confirming how a medical liquid was injected into a patient when the fluoroscopic image data of that patient was picked up.

Means for Solving Problem

According to the present invention, there is provided a fluoroscopic imaging system, comprising an imaging management unit that manages imaging order data to be used for picking up fluoroscopic image data of a patient; an imaging diagnostic apparatus that picks up the fluoroscopic image data of the patient according to the imaging order data; a data storage unit that stores therein the fluoroscopic image data to which at least a part of the imaging order data is allocated; a liquid injector that injects a medical liquid to the patient whose fluoroscopic image data is to be picked up and generates injection history data according to the injection; and a data control unit that registers the injection history data in the imaging management unit in association with the corresponding imaging order data.

With the fluoroscopic imaging system thus constructed, the injection history data is also stored in association with the imaging order data used for picking up the fluoroscopic image data, and therefore the injection history data can also be confirmed, for example based on the imaging order data.

The present invention provides a first data control unit, being the data control unit of the fluoroscopic imaging system according to the present invention, that registers the injection history data in the imaging management unit in association with the corresponding imaging order data. In the data control unit according to the present invention, therefore, the injection history data is associated with the imaging order data.

The present invention provides a second data control unit, being the data control unit of the fluoroscopic imaging system according to the present invention, comprising a history acquisition unit that acquires the injection history data from a liquid injector; an order acquisition unit that acquires, as the identification data, at least a part of the imaging order data corresponding to the injection history data, from at least one of the imaging management unit and the imaging diagnostic apparatus; an identification allocation unit that allocates the identification data to the injection history data; and a history transfer unit that outputs the injection history data allocated with the identification data to the imaging management unit. In the data control unit according to the present invention, therefore, the injection history data is associated with the imaging order data.

The present invention provides a first liquid injector, being the liquid injector of the fluoroscopic imaging system according to the present invention, comprising a liquid injection mechanism that injects a medical liquid into the patient who is to undergo the fluoroscopic image data pickup; a history generation unit that generates the injection history data corresponding to the liquid injection; and a history output unit that outputs the generated injection history data to the data control unit. In the liquid injector according to the present invention, therefore, the injection history data associated with the imaging order data is output to the data control unit.

The present invention provides a second liquid injector, being the liquid injector of the fluoroscopic imaging system according to the present invention, comprising a liquid injection mechanism that injects a medical liquid into the patient whose fluoroscopic image data is to be picked up; an injection control unit that variably adjusts an injection rate of the liquid with the lapse of time; a history generation unit that generates injection history data including a time-based graph in which one of the horizontal axis and the vertical axis represents the lapse of time and the other the injection rate; and history output unit that outputs the generated injection history data to the data control unit. In the liquid injector according to the present invention, therefore, the injection history data including the time-based graph of the injection rate and associated with the imaging order data is output to the data control unit.

It is to be noted that each constituent of the present invention has only to be capable of performing its function, and may be constituted in a form of, for example, an exclusive hardware that performs a predetermined function, a data processor in which a predetermined function is incorporated as a computer program, a predetermined function realized in a data processor by a computer program, and an optional combination thereof.

Also, the constituents of the present invention do not necessarily have to be individually independent, but may be configured such that a plurality of constituents constitutes a single member, a constituent is composed of a plurality of members, a constituent is a part of another constituent, a part of a constituent and a part of another constituent overlap, and so forth.

Effect of the Invention

In the fluoroscopic imaging system according to the present invention, the injection history data is also stored in association with the imaging order data to be stored, so that the injection history data can also be confirmed based on the imaging order data, and therefore it can be confirmed how a medical liquid was injected into the patient whose fluoroscopic image data was picked up.

In the data control unit according to the present invention, the injection history data is associated with the imaging order data, which enables viewing also the injection history data, based on the imaging order data.

With the liquid injector according to the present invention, the injection history data associated with the imaging order data is output to the data control unit, and hence the injection history data associated with the imaging order data can be provided to the data control unit.

BRIEF DESCRIPTION OF THE DRAWINGS

The above and other objects, features and advantages will become more apparent through a preferred embodiment described hereunder and the following accompanying drawings.

BEST MODE FOR CARRYING OUT THE INVENTION

Figure 1:
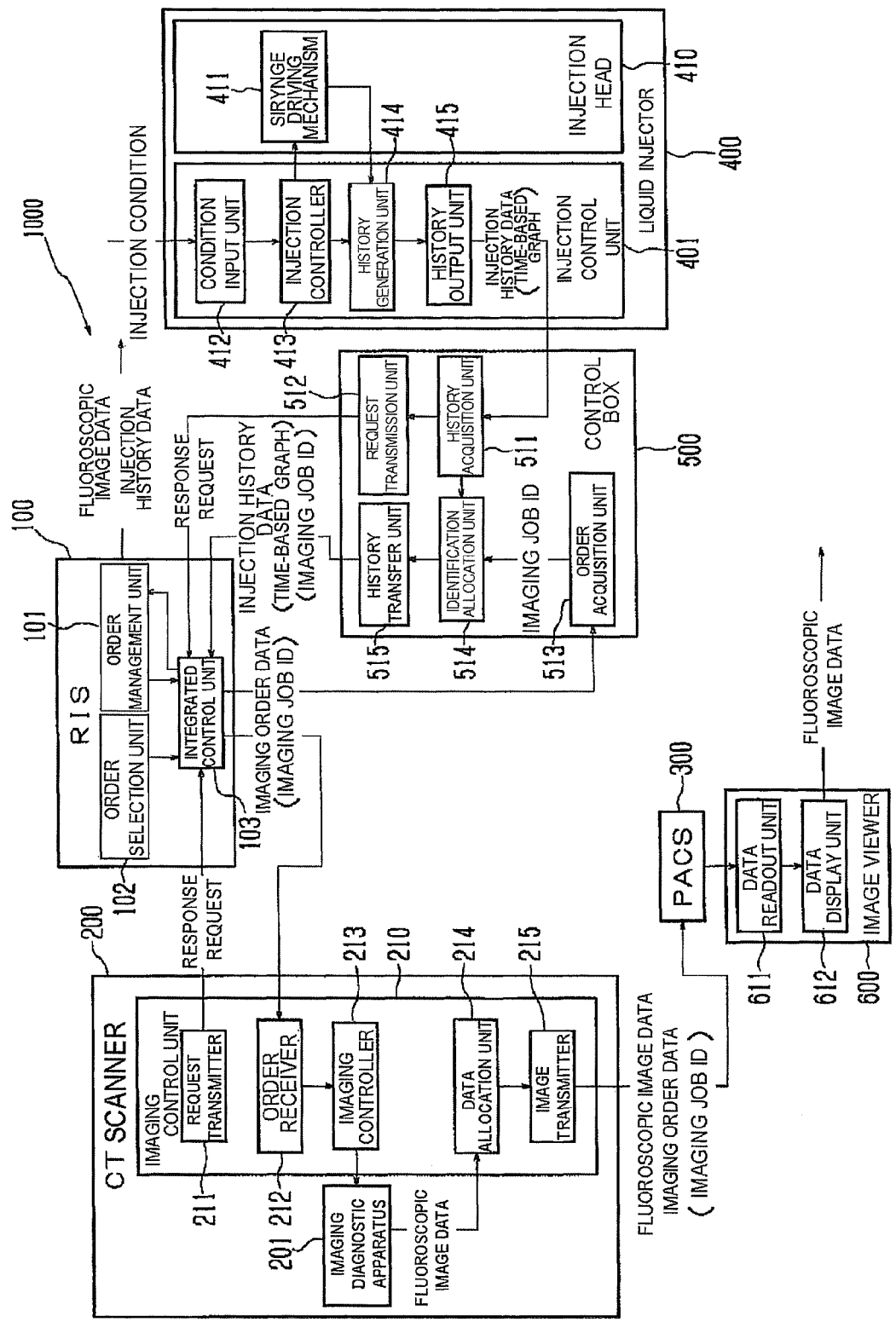
FIG. 1 is a schematic block diagram showing a logical structure of a fluoroscopic imaging system according to an embodiment of the present invention.
Figure 2:
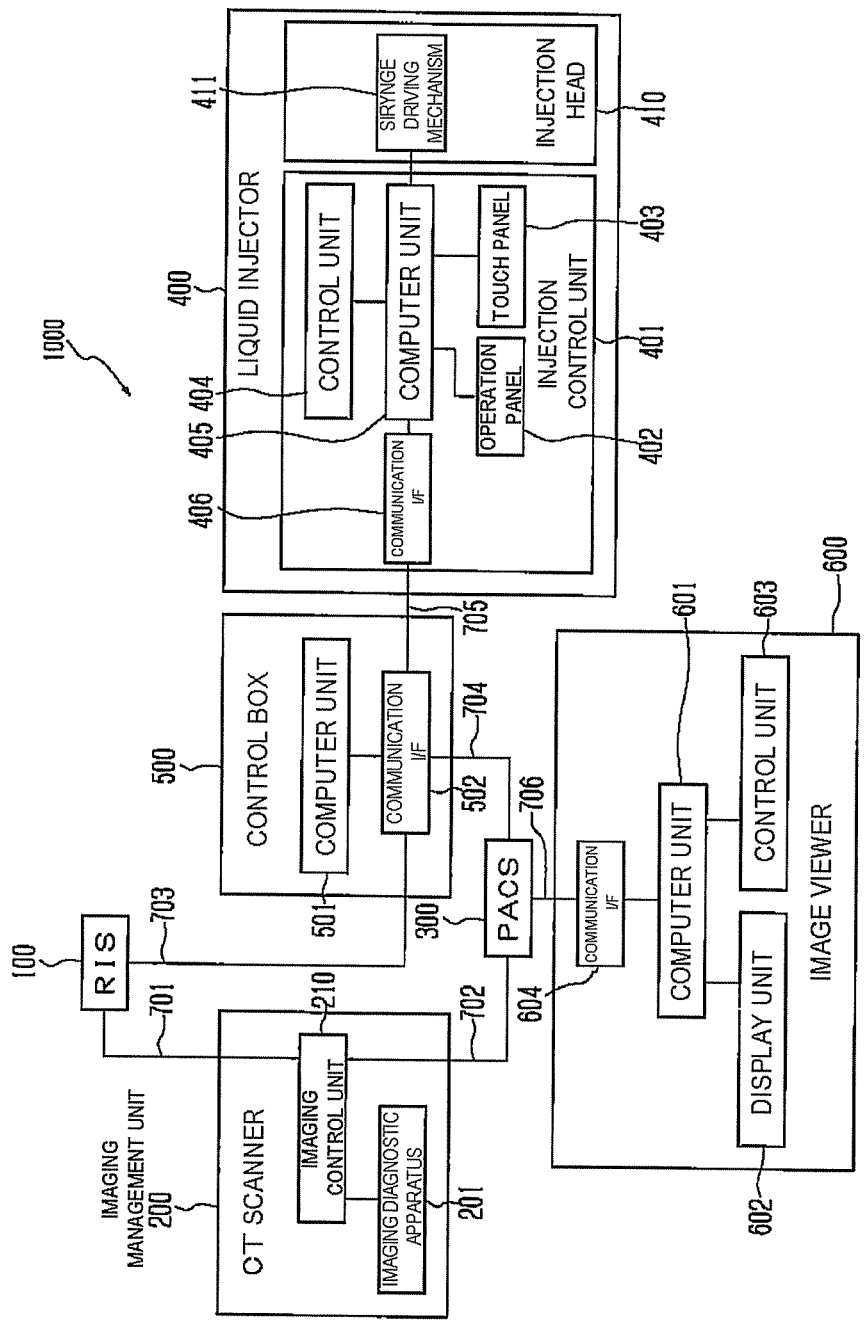
FIG. 2 is a block diagram showing a physical structure of the fluoroscopic imaging system.

Hereunder, an embodiment of the present invention will be described referring to the drawings. A fluoroscopic imaging system 1000 according to the embodiment of the present invention includes, as shown in FIGS. 1 and 2, a RIS 100 which serves as an imaging management unit, a CT scanner 200 which serves as an imaging diagnostic apparatus, a PACS 300 which serves as a data storage unit, a liquid injector 400, a control box 500 which serves as a data control unit, and an image viewer 600.

In the fluoroscopic imaging system 1000 according to this embodiment, the CT scanner 200 is connected to the RIS 100 and the PACS 300, through communication networks 701, 702 such as a Local Area Network (LAN), as illustrated.

The control box 500 is also connected to the RIS 100, the PACS 300, and the liquid injector 400 through communication networks 703 to 705. To the PACS 300, the image viewer 600 is connected through the communication network 706.

The fluoroscopic imaging system 1000 according to this embodiment is based on what is known as Digital Imaging and Communications in Medicine (DICOM). Accordingly, the respective units 100 to 600 of the fluoroscopic imaging system 1000 mutually communicate according to DICOM specification.

In the fluoroscopic imaging system 1000 according to this embodiment, one each of the CT scanner 200, the PACS 300, the liquid injector 400, and the control box 500 are provided, and all the combinations of these units are on a one-to-one basis.

The RIS 100 according to this embodiment is constituted of a known computer unit, in which an exclusive computer program is installed. In the RIS 100, an order management unit 101, an order selection unit 102, and an integrated control unit 103 are logically realized as the functions thereof, when the computer unit executes the corresponding processes according to the computer program.

The order management unit 101 corresponds to a storage device such as a hard disc drive (HDD), and serves to manage the imaging order data used for picking up fluoroscopic image data of the patient, in other words shooting a fluoroscopic image and thereby generating the fluoroscopic image data of the patient, with the exclusive identification data.

The imaging order data includes text data such as an imaging job ID which is the exclusive identification data, the identification data of the CT scanner 200, the identification data of the patient, and date and time of the start and finish of the imaging.

The order selection unit 102 corresponds to a function assigned to the central processing unit (hereinafter, CPU), including executing a predetermined process according to an input through a keyboard, and selects one from a plurality of imaging order data according to the input by the operator.

The integrated control unit 103 corresponds to a function assigned to the CPU including transmitting and receiving various data through a communication interface (I/F), and returns the selected one of the imaging order data according to a response request received from the CT scanner 200 or the control box 500.

The CT scanner 200 according to this embodiment includes, as shown in FIG. 2, a fluoroscopic imaging unit 201 which is the image-pickup execution mechanism, and an imaging control unit 210. The fluoroscopic imaging unit 201 shoots the fluoroscopic image data of the patient. The imaging control unit 210 controls the action of the fluoroscopic imaging unit 201.

To be more detailed, the imaging control unit 210 is constituted of a computer unit, in which an exclusive computer program is installed. In the imaging control unit 210, a request transmitter 211, an order receiver 212, an imaging controller 213, a data allocation unit 214, and an image transmitter 215 are logically realized as the functions thereof, when the computer unit executes the corresponding process according to the computer program.

The request transmitter 211 corresponds to a function assigned to the CPU including transmitting and receiving various data through the communication interface (I/F), and transmits the response request for the imaging order data to the RIS 100. The order receiver 212 receives the imaging order data returned from the RIS 100.

The imaging controller 213 controls the action of the fluoroscopic imaging unit 201 according to the imaging order data received. The data allocation unit 214 allocates the imaging order data to the fluoroscopic image data picked up by the fluoroscopic imaging unit 201.

The image transmitter 215 transmits the fluoroscopic image data allocated with the imaging order data to the PACS 300. Here, the fluoroscopic image data thus generated is composed of, for example, bit map data of the tomographic image.

The PACS 300 according to this embodiment is constituted of a database server, in which also an exclusive computer program is installed. The PACS 300 receives the fluoroscopic image data allocated with the imaging order data from the CT scanner 200, and stores the received data.

Figure 4:
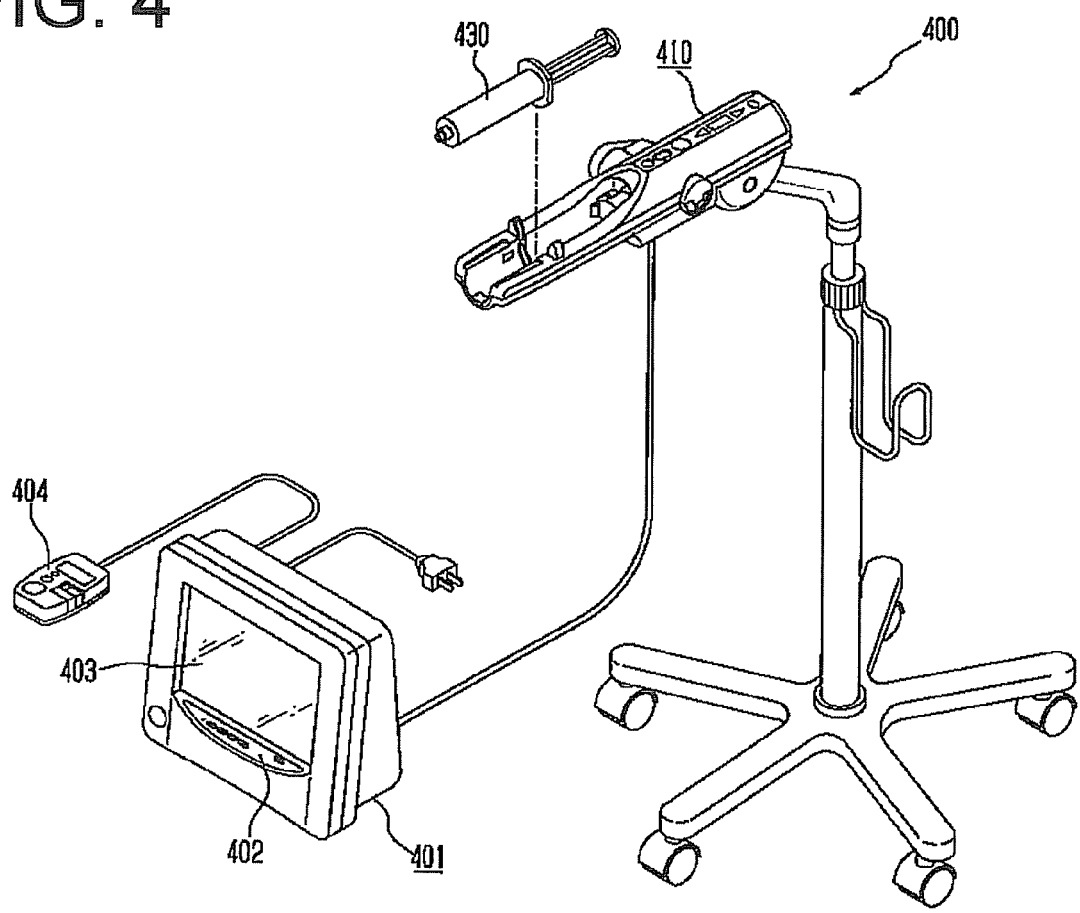
FIG. 4 is a perspective view showing the appearance of the liquid injector.
Figure 5:
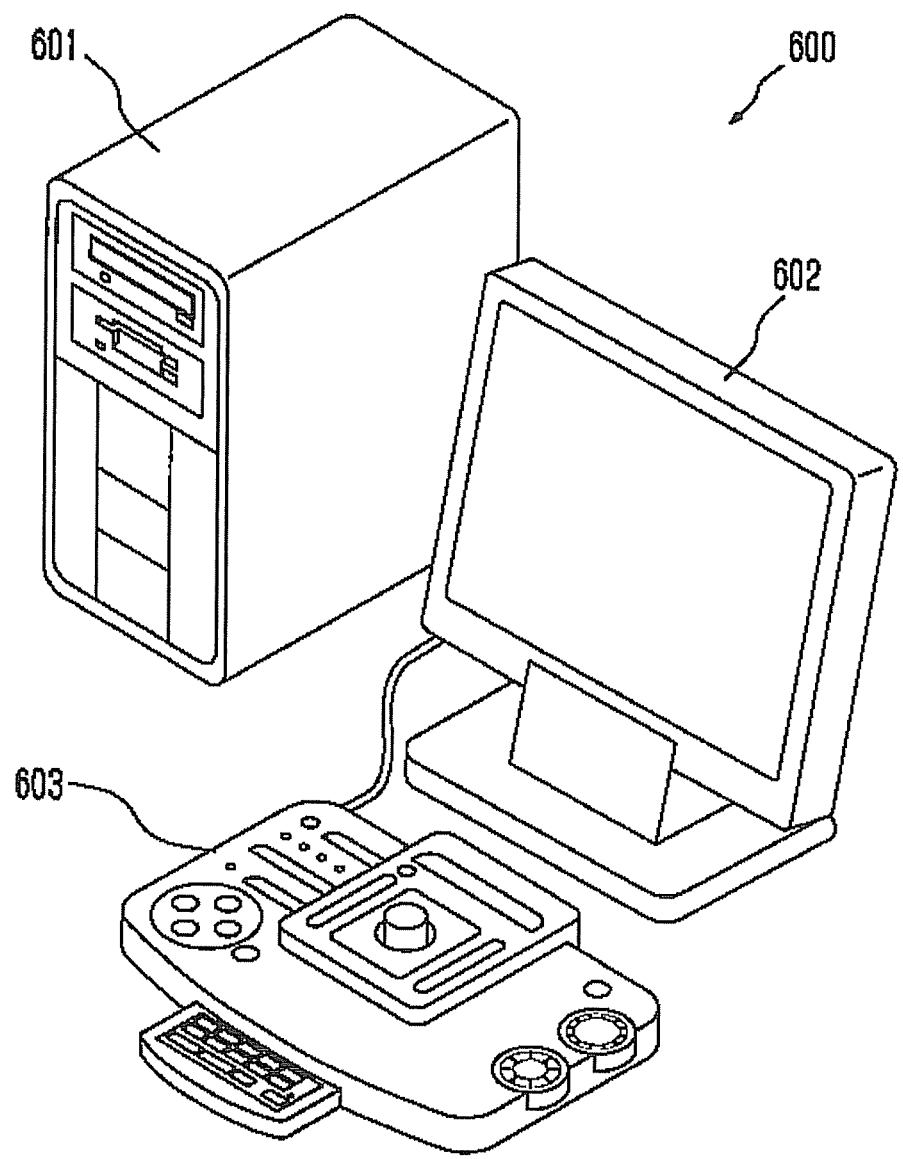
FIG. 5 is a perspective view showing an appearance of an image viewer.

The liquid injector 400 according to this embodiment includes, as shown in FIG. 4, an injection control unit 401 and an injection head 410. The injection control unit 401 controls the action of the injection head 410. The injection head 410 drives a liquid syringe 430 removably attached thereto, so as to inject a medical liquid (or simply liquid as the case may be), also called a medical fluid, into the patient.

To be more detailed, the injection control unit 401 includes, as shown in FIG. 2, an operation panel 402, a touch panel 403, a controller 404, a computer unit 405, a communication I/F 406. The injection head 410 includes a syringe driving mechanism 411, which is the liquid injection mechanism that drives the liquid syringe 430.

To the computer unit 405 of the liquid injector 400, the respective units cited above are connected. The computer unit 405 integrally controls the computer program, in which the respective units connected to the computer unit 405 are implemented.

Accordingly, in the liquid injector 400 according to this embodiment, units such as a condition input unit 412, an injection controller 413, a history generation unit 414, and a history output unit 415, are logically realized as the functions thereof, as shown in FIG. 1.

The condition input unit 412 corresponds to a function assigned to the computer unit 405, including detecting an input made through the operation panel 402 and the touch panel 403 according to the computer program, and accepts an input of the injection condition. The injection condition thus input includes identification data of the liquid, identification data of the region to be imaged, a target graph for variably adjusting the injection rate of the contrast medium, which is a medical liquid.

The injection controller 413 corresponds to a function assigned to the computer unit 405, including controlling the action of the syringe driving mechanism 411 according to the computer program and the data input to the operation panel 402, and variably adjusts the injection rate of the liquid from the syringe driving mechanism 411 with the lapse of time, according to the injection condition that has been input.

The history generation unit 414 corresponds to a function assigned to the computer unit 405, including executing a predetermined process according to the computer program, and generates the injection history data corresponding to the liquid injection.

The injection history data this generated includes text data such as an injection job ID which is exclusive identification data of each injection job, date and time of the start and finish of the injection, identification data of the liquid injector 400, and identification data of the liquid and the region to be imaged, which constitute the injection condition, and image data of the time-based graph in which one of the horizontal axis and the vertical axis represents the lapse of time and the other the injection rate.

The history output unit 415 corresponds to a function assigned to the computer unit 405 including executing data communication through the communication I/F 406, and transmits the generated injection history data to the control box 500.

The control box 500 according to this embodiment includes, as shown in FIG. 2, a computer unit 501 in which an exclusive computer program is installed, and a communication I/F 502.

In the control box 500, as shown in FIG. 1, units such as a history acquisition unit 511, a request transmission unit 512, an order acquisition unit 513, an identification allocation unit 514, and a history transfer unit 515, are logically realized as the function thereof, to be performed when the computer unit 501 executes the corresponding process according to the computer program.

The history acquisition unit 511 corresponds to a function assigned to the computer unit 501 including accepting reception data through the communication I/F 502, according to the computer program, and receives the injection history data from the liquid injector 400.

The request transmission unit 512 corresponds to a function assigned to the computer unit 501 including causing the communication I/F 502 to transmit the data according to the computer program, and transmits the response request for the imaging order data to the RIS 100 upon receipt of the injection history data.

The order acquisition unit 513 also corresponds to a function assigned to the computer unit 501 including accepting the reception data through the communication I/F 502, and receives the imaging order data the returned from the RIS 100.

The identification allocation unit 514 corresponds to a function assigned to the computer unit 501 including executing a predetermined process, and allocates the imaging job ID, the identification data exclusive to the imaging order data, to the injection history data.

The history transfer unit 515 corresponds to a function assigned to the computer unit 501 including causing the communication I/F 502 to transmit the data, and outputs the injection history data allocated with the imaging job ID, to the integrated control unit 103 of the RIS 100.

Accordingly, the integrated control unit 103 of the RIS 100 of this embodiment registers, upon receipt of the injection history data from the control box 500 as above, the injection history data together with the imaging job ID allocated thereto, in the order management unit 101.

Therefore, the order management unit 101 of the RIS 100 according to this embodiment not only manages the imaging order data as stated above, but also stores the injection history data. At this moment, the injection history data is stored in the RIS 100 in association with the imaging order data via the imaging job ID allocated to the injection history data.

The image viewer 600 according to this embodiment also includes a computer unit in which an exclusive computer program is installed. The image viewer 600 includes a computer unit 601, a display unit 602, a controller 603, a communication I/F 604, and so on.

In the image viewer 600 includes, as shown in FIG. 1, a data readout unit 611 and a data display unit 612, to be performed when the computer unit 601 executes the corresponding process according to the computer program.

The data readout unit 611 corresponds to a function assigned to the computer unit 601 including making access to the PACS 300 through the communication I/F 604 according to the computer program and the data input to the controller 603, and reads out the fluoroscopic image data from the PACS 300.

The data display unit 612 corresponds to the function assigned to the computer unit 601 including causing the display unit 602 to display the data received through the communication I/F 604, and displays the fluoroscopic image data and the injection history data that have been read out.

It is to be noted that the foregoing computer programs of the

RIS 100 are described as software for causing the RIS 100 to, for example, manage the imaging order data for picking up the fluoroscopic image data of the patient with the exclusive identification data, select one from a plurality of imaging order data according to an input by an operator, return the selected imaging order data according to the response request from the CT scanner 200 or the control box 500, receive the injection history data allocated with the imaging job ID of the imaging order data, from the control box 500, storing the injection history data thus received, in association with the imaging order data via the imaging job ID, and so forth.

The computer program of the CT scanner 200 is described as software for causing the imaging control unit 210 to, for example, transmit the response request for the imaging order data to the RIS 100 according to an input by the operator, receive the imaging order data returned from the RIS 100, control the action of the fluoroscopic imaging unit 201 according to the imaging order data that has been received, allocate the fluoroscopic image data picked up by the fluoroscopic imaging unit 201 with the imaging order data, and transmit the fluoroscopic image data allocated with the imaging order data to the PACS 300.

The computer program of the liquid injector 400 is described as software for causing the computer unit 405 to, for example, accept the input of the injection condition, variably adjust the injection rate of the liquid by the syringe driving mechanism 411 according to the injection condition that has been input, generate the injection history data including the time-based graph corresponding to the liquid injection, and transmit the generated injection history data to the control box 500.

The computer program of the control box 500 is described as software for causing the computer unit 501 to, for example, receive the injection history data from the liquid injector 400, transmit the response request for the imaging order data to the RIS 100 upon receipt of the injection history data, receive the imaging order data returned from the RIS 100, allocate the imaging job ID, which is the exclusive identification data of the imaging order data, to the injection history data, and output the injection history data allocated with the imaging job ID to the RIS 100.

The computer program of the PACS 300 is described as software for causing the PACS 300 to, for example, receive the fluoroscopic image data allocated with the imaging order data from the CT scanner 200 and store the fluoroscopic image data, and receive the injection history data allocated with the imaging job ID of the imaging order data from the control box 500, and store the injection history data.

The computer program of the image viewer 600 is described as software for causing the computer unit 601 to, for example, read out the fluoroscopic image data from the PACS 300, and display the fluoroscopic image data that has been read out.

Hereunder, a procedure of picking up the fluoroscopic image data of the patient with the fluoroscopic imaging system 1000 thus configured according to this embodiment will be sequentially described. To start with, the operator registers in advance the imaging order data in the RIS 100. Accordingly, the operator engaged in executing the imaging job can select one of the imaging order data corresponding to the ongoing imaging job, by manually operating the RIS 100.

The imaging order data is composed of the text data including the imaging job ID, the identification data of the CT scanner 200, the identification data of the patient, and date and time of the start and finish of the imaging. In other words, the imaging order data includes those data necessary for the CT scanner 200 to execute the imaging job, but does not include the data that enables identifying the injection job of the liquid injector 400.

Figure 3:
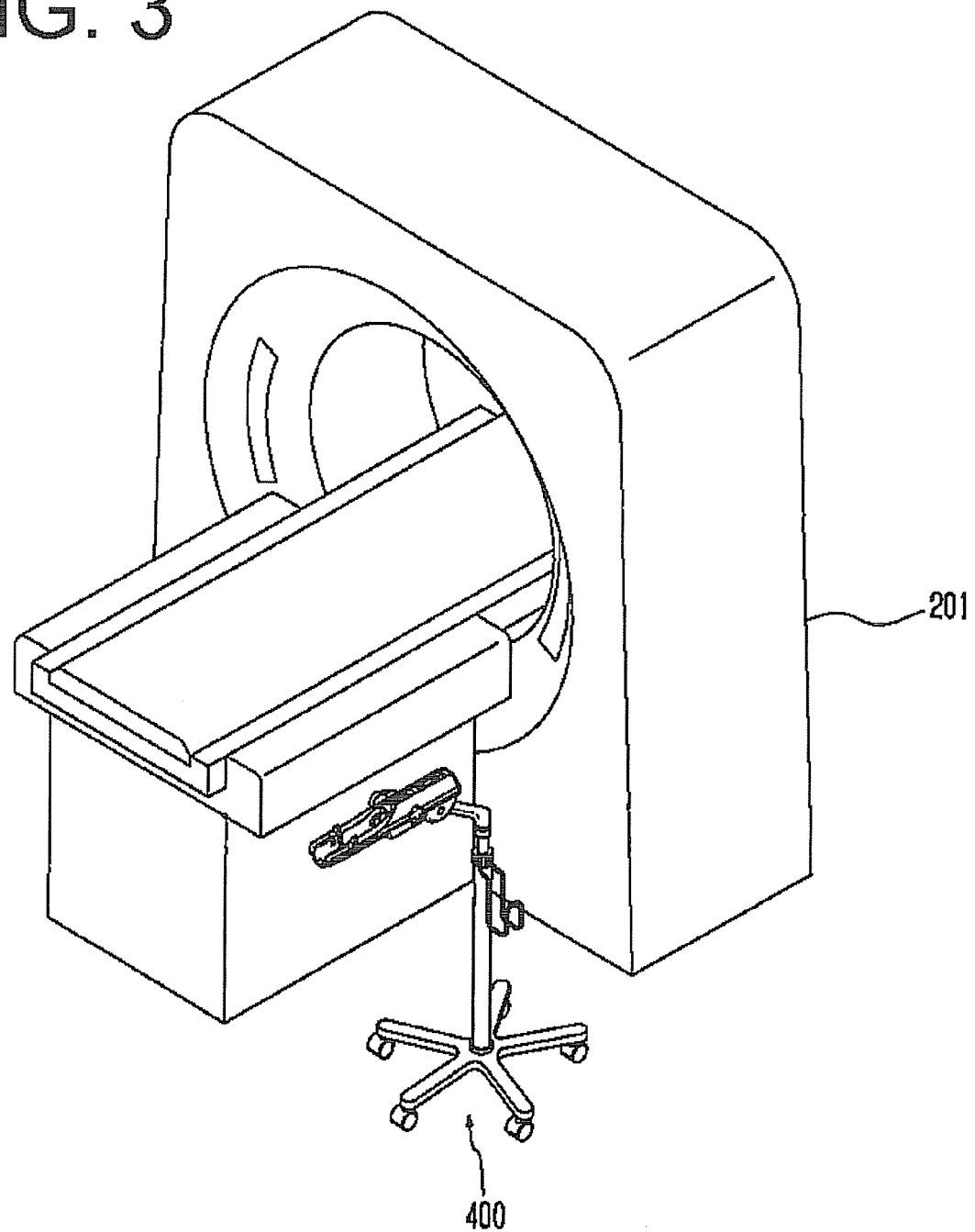
FIG. 3 is a perspective view showing an appearance of a fluoroscopic imaging unit of a CT scanner and an injection head of a liquid injector.

Meanwhile at the actual site of the imaging job, the liquid injector 400 is located close to the fluoroscopic imaging unit 201 of the CT scanner 200, as shown in FIG. 3. Then the liquid syringe 430 is connected to the patient in the imaging unit 301 (not shown) through an extension tube, and the liquid syringe 430 is loaded onto the injection head 410 of the liquid injector 400.

Figure 6:
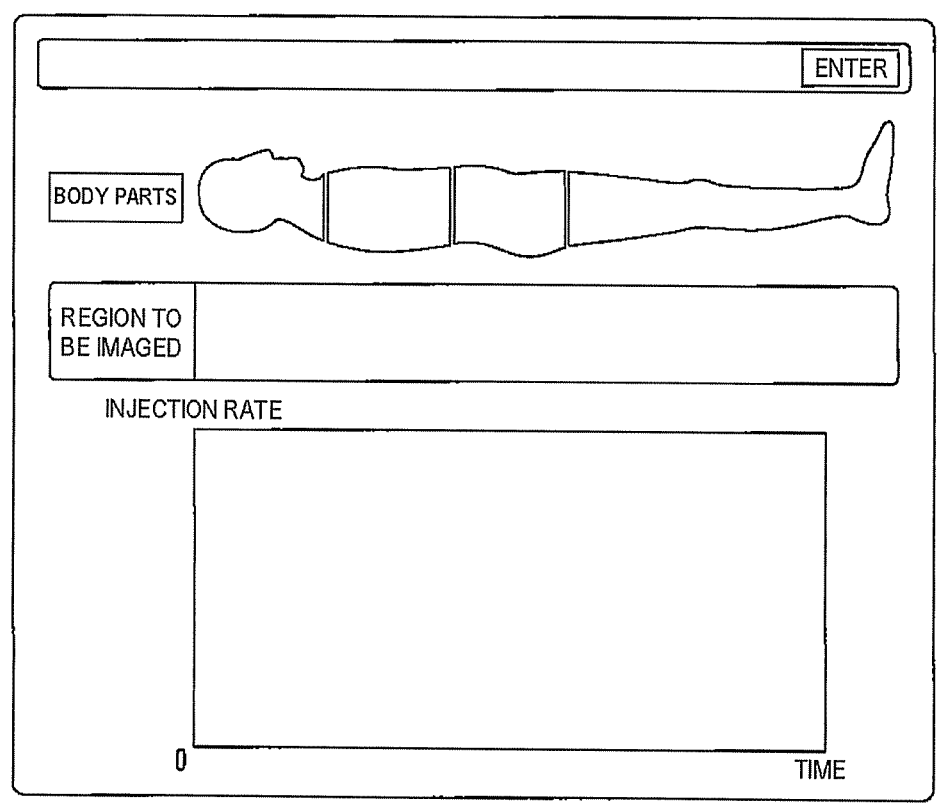
FIG. 6 is a schematic front view showing a screen of the liquid injector, displaying a simulated image of body parts and condition columns in blank.

Once the operator activates the liquid injector 400 for example by an inputting action through the operation panel 402 of the injection control unit 401, a simulated image of a plurality of body parts is displayed in an upper portion of the touch panel 403, as shown in FIG. 6.

Below the simulated image, a selection screen of the region to be imaged is displayed, in a horizontally slender rectangular shape. In a lower portion of the touch panel 403, a horizontally stretched rectangular-shaped condition screen is displayed, a vertical axis of which represents the injection rate of the liquid, and a horizontal axis the injection time. Under such state, the operator inputs, for example, the identification data of the liquid and that of the region to be imaged through the operation panel 402, as apart of the injection condition.

Figure 7:
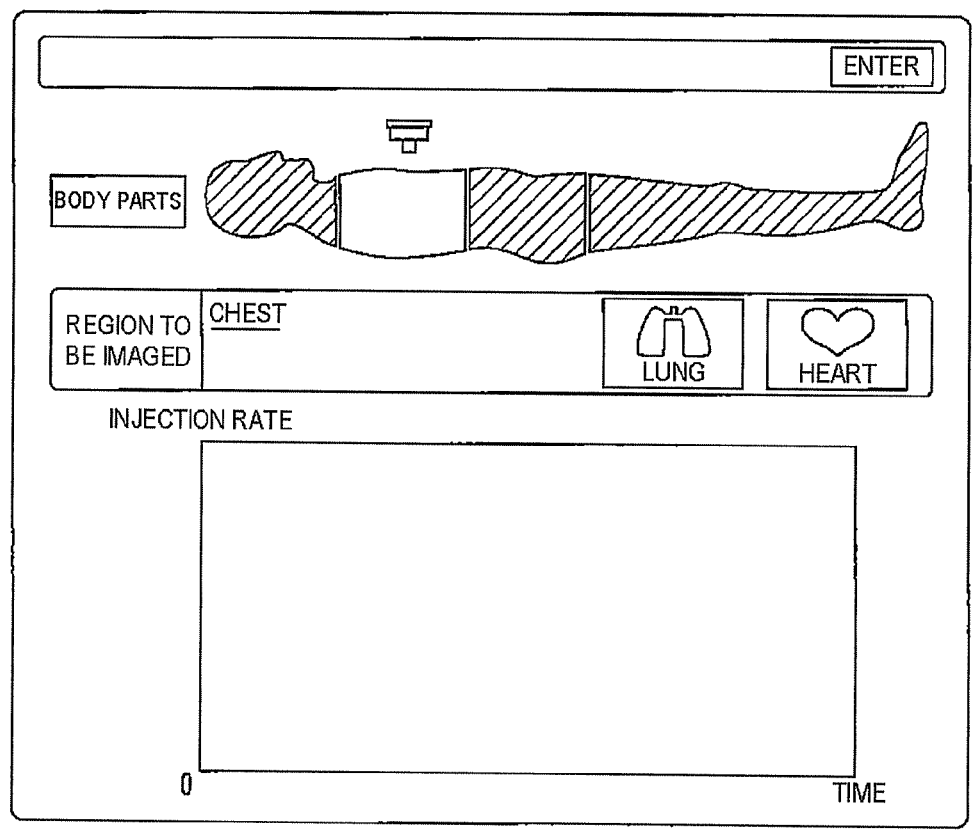
FIG. 7 is a schematic front view showing the screen displaying a state where a body part has been selected.

The operator then presses with a finger one of the plurality of body parts of the simulated image displayed on the touch panel 403. Then only the selected part of the simulated image is lit up while all the remaining parts are turned off, as shown in FIG. 7, and an icon of the scanner mechanism is displayed above the selected part of the simulated image.

Figure 8:
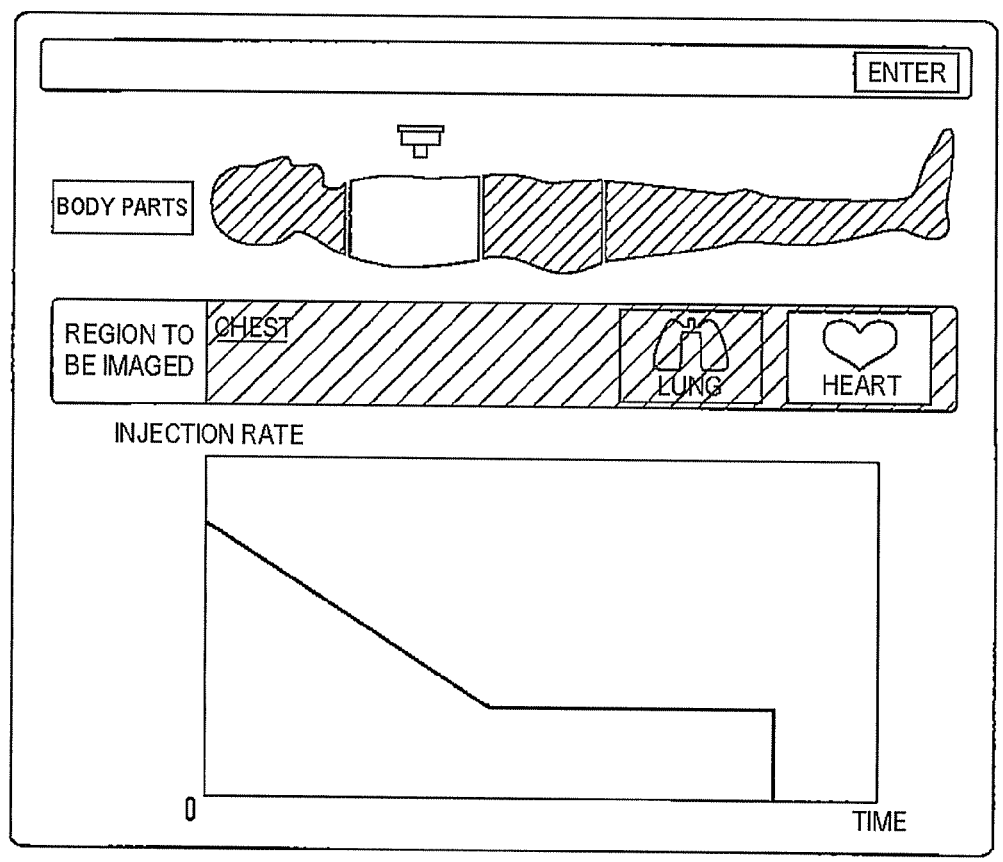
FIG. 8 is a schematic front view showing the screen displaying the selected region to be imaged and a target graph.

At the same time, below the selected part, icons of a plurality of regions to be imaged corresponding to the selected body part is read out and displayed in the selection screen. When the operator inputs one of the icons by pressing with a finger, only the selected icon is lit up and the others are turned out, as shown in FIG. 8.

Once the region to be imaged is thus selected, the target graph corresponding to the region to be imaged is read out and set as the injection condition by the computer unit 405, in the liquid injector 400 of this embodiment.

The target graph is then displayed as the target to be followed up, in the condition screen on the touch panel 403. Once the start of the injection is input under such state, the liquid injector 400 controls, upon detecting the input, the action of the syringe driving mechanism 411 according to the target graph to be followed, to thereby inject the contrast medium into the patient.

In this process, the lapse of time is measured on a real time basis and the actual injection rate is detected, so that a feedback control is executed upon the syringe driving mechanism 411 such that the injection rate agrees with the target graph.

Figure 9:
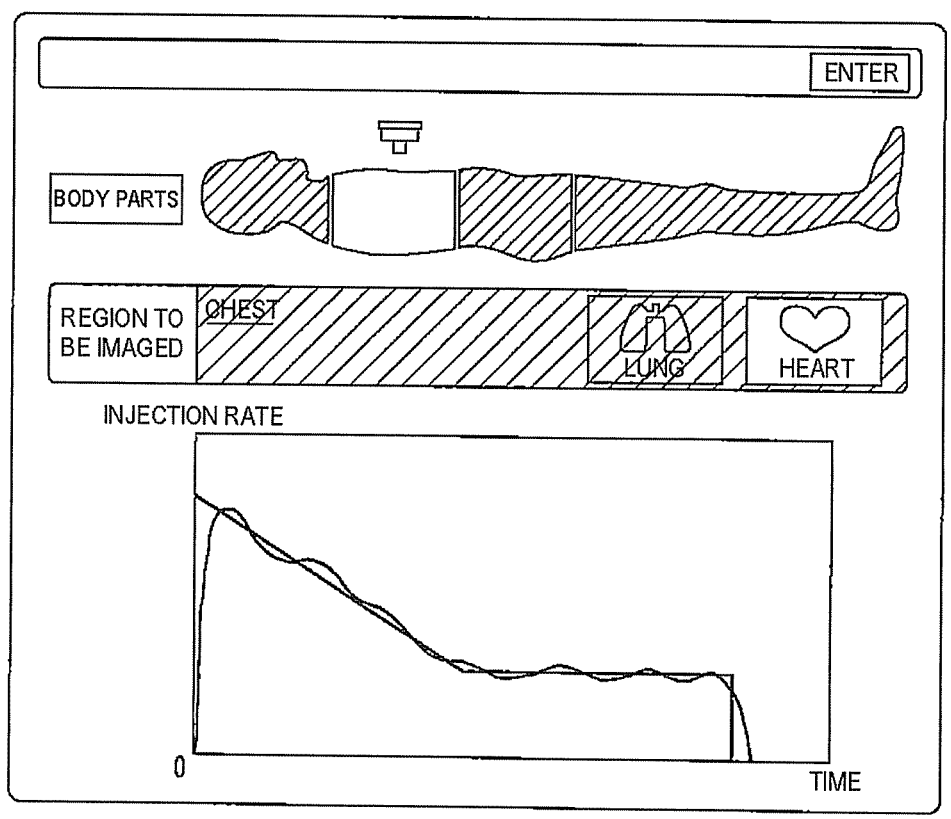
FIG. 9 is a schematic front view showing the screen of the liquid injector, displaying the target graph and a time-based graph.

Also, the time-based graph indicating the actual injection rate is generated on a real time basis, and is displayed with the target graph on the touch panel 403 as shown in FIG. 9. When the injection job is completed, the injection history data including the time-based graph corresponding to the actual injection rate is generated.

The injection history data thus generated is composed of the text data including the injection job ID, the date and time of the injection job, the identification data of the liquid injector 400, that of the liquid, and that of the region to be imaged, and the image data of the foregoing time-based graph. In other words, the injection history data includes those data necessary for confirming the details of the injection job executed by the, but does not include the data that enables identifying the imaging order data.

Upon completing the injection job, the liquid injector 400 transmits the generated imaging order data to the control box 500. The control box 500 transmits, upon receipt of the imaging order data from the liquid injector 400, the response request for the imaging order data to the RIS 100.

The RIS 100 then returns the imaging order data selected as already described to the control box 500. The control box 500 extracts, upon receipt of the imaging order data from the RIS 100, the imaging job ID of the imaging order data and allocates such ID to the injection history data.

Then the control box 500 transmits the injection history data allocated with the imaging job ID to the RIS 100. The RIS 100 stores the received injection history data, utilizing the imaging job ID as the index.

Thus, the imaging order data and the injection history data can be managed in mutual association via the imaging job ID, since the RIS 100 manages the imaging order data based on the imaging job ID as stated above.

Meanwhile, in a normal operation, around the time when the liquid injector 400 completes the injection job as above, the imaging job by the CT scanner 200 is started. In this case, the operator inputs the start of the imaging job to the imaging control unit 210 of the CT scanner 200.

The imaging control unit 210 of the CT scanner 200 then transmits the response request for the imaging order data to the RIS 100. The
RIS 100 returns the imaging order data selected as above to the CT scanner 200.

The CT scanner 200 controls the action of the fluoroscopic imaging unit 201 according to the imaging order data received by the imaging control unit 210, so that the fluoroscopic image executes the imaging job.

Thereafter, once the fluoroscopic imaging unit 201 picks up the fluoroscopic image data of the patient, the imaging control unit 210 allocates the fluoroscopic image data with the imaging order data. The imaging control unit 210 then transmits the fluoroscopic image data allocated with the imaging order data to the PACS 300.

The PACS 300 stores the fluoroscopic image data, utilizing the imaging job ID of the imaging order data as the index. When the operator is to review the fluoroscopic image data, the operator may manually operate, for example, the image viewer 600, to thereby read out the fluoroscopic image data from the PACS 300.

In this case, inputting for example the imaging job ID as the retrieval key causes the fluoroscopic image data corresponding to that imaging job ID to be read out from the PACS 300, and to be displayed on the display unit 602 of the image viewer 600.

As stated above, in the fluoroscopic imaging system 1000 according to this embodiment, the RIS 100 manages the imaging order data and the injection history data in mutual association via the imaging job ID. Such arrangement allows even confirming with the RIS 100 how a medical liquid was injected into the patient whose fluoroscopic image data was picked up.

In particular, in the fluoroscopic imaging system 1000 according to this embodiment, the fluoroscopic image data picked up by the CT scanner 200 and stored in the PACS 300 is also allocated with the imaging order data. Such arrangement enables associating the fluoroscopic image data with the injection history data, via the imaging job ID.

Moreover, in the fluoroscopic imaging system 1000 according to this embodiment, the liquid injector 400 variably adjusts the injection rate of the contrast medium in order to upgrade the quality of the fluoroscopic image data to be picked up by the CT scanner 200. Also, since the time-based graph corresponding to the injection rate is included in the injection history data, the injection process of the contrast medium can be confirmed in details.

In the case where the injection job of the contrast medium turns to be suspicious, the injection history data can be employed as the evidence, because the injection history data can also be confirmed together with the fluoroscopic image data.

In particular, the units 100 to 600 of the fluoroscopic imaging system 1000 according to this embodiment mutually execute the data communication in accordance with the DICOM standards. Since it is difficult to falsify the communication data according to DICOM, the injection history data has high admissibility as evidence.

Also, in the case of picking up the fluoroscopic image data of the same patient again, the previous injection history data can be referred to. Accordingly, the appropriate injection condition can be easily input into the liquid injector 400.

In the case of picking up the fluoroscopic image data again, particularly from a patient whose weight has been fluctuating because of the progress of the disease, reviewing the previous fluoroscopic image data and the injection history data allows simply inputting the appropriate injection condition into the liquid injector 400.

Also, in this embodiment the injection history data includes the time-based graph. Accordingly, even though the injection condition is so complicated as to correct the target graph along which the injection rate is to be variably adjusted, the injection condition can be simply input into the liquid injector 400.

Further, in the fluoroscopic imaging system 1000 according to this embodiment, the injection history data including the text data such as the injection condition is stored in the RIS 100. Such arrangement allows the RIS 100 to generate, for example, various statistical data related to the liquid injection, from the numerous injection history data accumulated.

Particularly, since the injection history data is stored together with the imaging order data and so on, various statistical data related to the liquid injection can be generated together with the imaging condition and so on included in the imaging order data.

Here, in the fluoroscopic imaging system 1000 according to this embodiment, the imaging order data and the fluoroscopic image data do not include, as in the conventional system, those data that allows identifying the injection condition input to the liquid injector 400 and the generated injection history data.

Likewise, the injection condition input to the liquid injector 400 and the generated injection history data do not include either, those data that permits identifying the imaging order data and the fluoroscopic image data. In other words, the imaging order data cannot be identified from the injection history data, as in the conventional system.

Normally, however, the imaging job by the CT scanner 200 is started around the time when the liquid injector 400 completes the injection job. Also, by the time that the CT scanner 200 starts the imaging job, one imaging order data is selected in the RIS 100.

Accordingly, in consideration of such situation, in the fluoroscopic imaging system 1000 according to this embodiment, the control box 500 acquires the imaging order data at the time when the injection history data is input. Such arrangement allows the control box 500 to acquire the proper without executing data retrieval or data look-up, so as to allocate the imaging order data to the injection history data.

Further, in the fluoroscopic imaging system 1000 according to this embodiment, the control box 500 only extracts the imaging job ID from the imaging order data, and allocates such ID to the injection history data. Such arrangement assures the association of the injection history data with the fluoroscopic image data, with a minimal necessary data capacity.

It is to be noted that the present invention is not in any way limited to the foregoing embodiment, but allows various modifications within the scope of the present invention. For example, the above embodiment represents the case where the fluoroscopic imaging system 1000 includes one each of the respective units, for the sake of explicitness of the description.

However, in a large-scaled hospital or the like, each of a plurality of fluoroscopic imaging systems may include one each of the RIS 100, the CT scanner 200, the liquid injector 400, and the control box 500, and the plurality of fluoroscopic imaging systems may share the PACS 300 and the image viewer 600 (not shown). In such case also, the hardware such as the RIS 100, the PACS 300, and the image viewer 600 maybe prepared in a plurality of numbers and connected in parallel (not shown).

Also, the foregoing embodiment represents the case where the fluoroscopic image data and the injection history data are stored in a single unit of the PACS 300. However, the hardware that stores the fluoroscopic image data and the hardware that stores the injection history data may be independently prepared and connected via the communication network.

The foregoing embodiment represents the case where the RIS 100, the CT scanner 200, the PACS 300, the liquid injector 400, the control box 500, and the image viewer 600 are separately formed and mutually connected via the communication network 701 to 706.

However, the respective units 200 to 600 may be integrally constituted in various combinations. To cite a few examples, the injection control unit 401 of the liquid injector 400 and the control box 500 may be integrally constituted; the RIS 100 and the PACS 300 may be added to such combination to thereby form a unified structure; and the PACS 300 and the image viewer 600 may be integrally constituted.

Also, the control box 500 may be unified with the RIS 100 and the PACS 300, and the control box 500, the PACS 30, and the image viewer 600 may be integrally constituted.

Further, the imaging control unit 210 of the CT scanner 200, the RIS 100, and the control box 500 may be integrally constituted; the imaging control unit 210 of the CT scanner 200, the PACS 300, and the control box 500 may be integrally constituted; and the image viewer 600 may be added to thereby form a unified structure.

Further, the image viewer 600 and the PACS 300 may be integrally constituted; and the control box 500, and the imaging control unit 210 of the CT scanner 200 may be added to thereby form a unified structure.

The foregoing embodiment represents the case where the entirety of the imaging order data is allocated to the fluoroscopic image data, and stored in the PACS 300. However, only the imaging job ID may be allocated to the fluoroscopic image data, from the imaging order data.

Also, only the imaging job ID out of the imaging order data may be allocated to the fluoroscopic image data, while allocating the entirety of the imaging order data to the injection history data, and the imaging order data may be dividedly allocated to the fluoroscopic image data and the injection history data.

Further, the injection history data may include both of the time-based graph and the target graph. The entire display content on the touch panel 403 of the liquid injector 400 may be included in the injection history data.

The foregoing embodiment represents the case where the injection history data is composed of the text data including the injection job ID, date and time and so on, and the image data including the time-based graph of the injection rate. However, the injection history data may only contain the text data.

In particular, the foregoing embodiment represents the case where the liquid injector 400 variably adjusts the injection rate of the contrast medium, and stores the corresponding time-based graph as apart of the injection history data. However, the liquid injector 400 may inject the contrast medium at a constant rate. In this case, it barely makes sense to generate the time-based graph and store the same. Accordingly, it is more preferable to include the injection rate in a form of the text data in the injection history data.

The foregoing embodiment represents the case where the control box 500 acquires the imaging order data from the RIS 100 upon receipt of the injection history data from the liquid injector 400. However, the liquid injector 400 may notify the control box 500 of the start and finish of the injection job, so that the control box 500 acquires the imaging order data from the RIS 100, upon receipt of such notice. Such arrangement allows the control box 500 to acquire the proper imaging order data, even in the case where the liquid injection and the fluoroscopic image pickup are executed at the same time.

Also, the control box 500 may acquire the imaging order data from the RIS 100 a predetermined time after the receipt of the injection history data or the notice of the start or finish. Such arrangement allows the control box 500 to acquire the proper imaging order data, even though the imaging job of the fluoroscopic image is started, a predetermined time after the completion of the liquid injection job.

Likewise, the liquid injector 400 may notify the control box 500 of the start and finish of the liquid injection after a predetermined time, so that the control box 500 transmits the response request upon receipt of the notice from the liquid injector 400.

Further, the CT scanner 200 may notify the control box 500 of the start and finish of the imaging job, so that the control box 500 acquires the imaging order data from the RIS 100.

Further, the control box 500 may acquire the imaging order data from the RIS 100 a predetermined time after the receipt of the imaging history data or the notice of the start and finish. Likewise, the CT scanner 200 may notify the control box 500 of the start and finish of the imaging of the liquid after a predetermined time, so that the control box 500 transmits the response request upon receipt of the notice from the CT scanner 200.

Still further, the control box 500 which has received the notice of the start and finish of the injection from the liquid injector 400 as above may notify the RIS 100 of such start and finish. Such arrangement allows the RIS 100 to notify the CT scanner 200 of the start time and the finish time of the liquid injection, together with the imaging order data and so on.

Accordingly, the operator handling the CT scanner 200 can refer to the start time and the finish time of the liquid injection, and hence the operator can adjust the start time of the image pickup, according to the time of the liquid injection.

Likewise, the liquid injector 400 may notify the control box 500 of the injection condition, and the injection condition may be notified to the RIS 100 by the control box 500. In this case, the injection condition can be notified to the CT scanner 200 from the RIS 100, together with the imaging order data and so on.

Such arrangement allows the operator handling the CT scanner 200 to refer to the injection condition, thereby facilitating the operator to adjust the imaging action according to the injection condition. It is also feasible to automatically control the imaging action based on the injection condition acquired by the imaging control unit 210 of the CT scanner 200.

The foregoing embodiment represents the case where the liquid injector 400 transmits the injection history data, upon completion thereof, to the control box 500. However, the liquid injector 400 may transmit the injection history data in separate portions to the control box 500, so that the control box 500 unifies the injection history data.

To be more detailed, the liquid injector 400 may transmit, upon starting the injection, the injection condition and the date and time of the start of the injection to the control box 500; sequentially transmit the injection rate and so on during the injection process; and transmit the finish time upon completing the injection. In this case, the control box 500 can complete the injection history data from various data accumulated during the injection process, and output the completed data.

The foregoing embodiment represents the case where the liquid injector 400 injects only the contrast medium into the patient with a single liquid syringe 430. However, the liquid injector may employ a plurality of liquid syringes so as to inject the contrast medium and physiological saline as the medical liquid or medical fluid, into the subject (not shown).

For example, in the case where the liquid injector is to sequentially inject the contrast medium and the physiological saline as the medical liquid into the patient, at least one of the finish of the injection of the contrast medium and the start of the injection of the physiological saline may be notified to the control box 500.

Alternatively, the liquid injector set to sequentially inject the contrast medium and the physiological saline as the medical liquid into the patient may transmit the injection history data of the contrast medium to the control box 500, upon completion of the injection of the contrast medium.

The foregoing embodiment represents the case where the RIS 100 is of the push-type, and the control box 500 acquires the proper imaging order data at a predetermined timing. However, the RIS 100 may be of the pull-type.

In the latter case, the CT scanner 200 transmits the response request for the imaging order data to the RIS 100 with at least an order retrieval key. Then the RIS 100 selects one of the plurality of imaging order data according to the response request and the order retrieval key received from the CT scanner 200, and returns the selected data.

The control box 500 then transmits the response request for the imaging order data to the RIS 100 at a predetermined timing corresponding to the liquid injection. The RIS 100 returns the selected imaging order data according to the response request received from the control box 500.

Alternatively, the RIS 100 may return a plurality of imaging order data according to the response request received from the CT scanner 200. In this case, the CT scanner 200 accepts an operation of selecting one of the plurality of imaging order data returned, and notifies the RIS 100 of the selected imaging order data.

The RIS 100 may also retrieve a part of the plurality of imaging order data based on the response request and the order retrieval key received from the CT scanner 200, and return the retrieved data. The CT scanner 200 accepts an operation of selecting one of the imaging order data returned, and notifies the RIS 100 of the selected imaging order data.

Once the control box 500 transmits the response request for the imaging order data to the RIS at a predetermined timing corresponding to the liquid injection, the RIS 100 returns the one of the imaging order data notified of by the CT scanner 200, according to the response request received from the control box 500.

Such arrangement allows the control box 500 to acquire the proper imaging order data despite that the RIS 100 is of the pull-type, and to allocate the imaging job ID and so on to the injection history data.

The foregoing embodiment represents the case where the control box 500 unconditionally acquires the imaging order data provided by the RIS 100. However, the control box 500 may transmit the response request for the imaging order data to the RIS 100 with at least an order retrieval key.

In this case, the RIS 100 retrieves a part of the plurality of imaging order data according to the order retrieval key received from the control box 500, and if the retrieved imaging order data includes the one notified of by the CT scanner 200, the RIS 100 returns that one. Such arrangement further assures that the control box 500 acquires the proper imaging order data.

Here, in the foregoing case, the liquid injector 400 may transmit the generated injection history data to the control box 500, so that the control box 500 may transmit at least a part of the received injection history data to the RIS 100, as the order retrieval key.

Such arrangement allows the control box 500 to generate the proper order retrieval key from the injection history data, and to thereby allocate the proper imaging order data to the injection history data.

The foregoing embodiment represents the case where the control box 500 acquires the imaging order data from the RIS 100. However, the RIS 100 and the CT scanner 200 may be connected via the control box 500, so that the control box 500 may acquire the imaging order data which is transmitted from the RIS 100 to the CT scanner 200.

Also, the control box 500 may acquire the imaging order data from the CT scanner 200. In this case, for example, the control box 500 may transmit the response request for the imaging order data to the CT scanner 200 at the predetermined timing corresponding to the liquid injection, and the CT scanner 200 may return the imaging order data according to the response request received from the control box 500.

Alternatively, the CT scanner 200 may transfer the imaging order data returned from the RIS 100 to the control box 500. Further, the CT scanner 200 may accept an operation of selecting one of the plurality of imaging order data returned from the pull-type RIS 100, to thereby transfer the selected imaging order data to the control box 500.

The foregoing embodiment represents the case where the control box 500 acquires one of the imaging order data selected by the RIS 100, and transmits the injection history data to the RIS 100, upon allocating the imaging job ID of that imaging order data to the injection history data.

However, the control box 500 may transmit the injection history data to the RIS 100 where one of the imaging order data is selected, so that the RIS 100 may store the received injection history data in association with the selected imaging order data.

Likewise, in the configuration where the control box 500 transmits the injection history data to the RIS 100 without acquiring the imaging order data as above so that the RIS 100 may store the injection history data, the RIS 100 may be of the pull-type.

In this case, the CT scanner 200 transmits the response request for the imaging order data to the RIS 100, with at least one order retrieval key. The RIS 100 then selects and returns one of the plurality of imaging order data according to the response request received from the CT scanner 200 and the order retrieval key.

Then the control box 500 transmits the injection history data to the RIS 100 at a predetermined timing corresponding to the injection of the liquid. The RIS 100 stores the injection history data received from the control box 500, in association with the selected one of the imaging order data.

Alternatively, the RIS 100 may return the plurality of imaging order data according to the response request received from the CT scanner 200. In this case, the CT scanner 200 accepts an operation of selecting one of the plurality of imaging order data returned, and notifies the RIS 100 of the selected imaging order data.

Alternatively, the RIS 100 may retrieve and return a part of the plurality of imaging order data according to the response request received from the CT scanner 200 and the order retrieval key. The CT scanner 200 then accepts the operation of selecting one of the imaging order data returned, and notifies the RIS 100 of the selected imaging order data.

Then once the control box 500 transmits the injection history data to the RIS 100 at the predetermined timing corresponding to the injection of the liquid, the RIS 100 stores the injection history data received from the control box 500, in association with the selected one of the imaging order data.

The foregoing arrangement enables the RIS 100 to store the injection history data received from the control box 500 in association with one of the imaging order data, also in the case where the RIS 100 is of the pull-type.

Alternatively, the control box 500 may transmit the injection history data to the RIS 100 with at least one order retrieval key.

In this case, the RIS 100 retrieves apart of the plurality of imaging order data according to the order retrieval key received from the control box 500, and stores, in the case where the part of the imaging order data thus retrieved includes the one notified of by the CT scanner 200, that imaging order data in association with the injection history data.

The foregoing embodiment represents the case where the CT scanner 200 serves as the imaging diagnostic apparatus, and the liquid injector 400 injects the contrast medium as the medical liquid, for CT scanning. However, a MRI equipment, a PET equipment, or an ultrasonic diagnostic equipment may be employed as the imaging diagnostic apparatus, and the liquid injector may inject the contrast medium prepared exclusively for such equipments.

Also, the foregoing embodiment represents the case where the CT scanner 200 and the liquid injector 400 are independently activated on a stand-alone basis. However, the CT scanner 200 and the liquid injector 400 may work in correlation to perform various actions, through data communication.

Further, the foregoing embodiment represents the case where the respective units 100 to 600 mutually perform the data communication according to DICOM standards which is difficult to falsify, thereby securing high admissibility of the injection history data as evidence. However, the liquid injector 400 may generate the injection history data in a data format difficult to falsify, such as the Portable Document Format (PDF).

Likewise, the control box 500 may convert the injection history data received from the liquid injector 400 in the Joint Photographic Coding Experts Group (JPEG) format into the PDF format. Further, the liquid injector 400 and the control box 500 may be connected to what is known as the Internet, so as to acquire an electronic signature and allocate the injection history data with the same.

Still further, the foregoing embodiment represents the case where the computer unit works according to the computer program, to thereby logically realize the respective units 100 to 600 to perform the assigned functions. However, it is also possible to set up the respective units as individually independent hardware, or some units as hardware and the others as software.

Naturally, the foregoing structures may be combined in various manners, unless contradiction is incurred.

The invention claimed is:

1. A fluoroscopic imaging system, comprising:
    a first computer that manages imaging order data to be used for picking up fluoroscopic image data of a patient;
    an imaging diagnostic apparatus that picks up the fluoroscopic image data of the patient according to the imaging order data;
    a database server that stores therein the fluoroscopic image data to which at least a part of the imaging order data is allocated;
    a liquid injector adapted to inject a medical liquid to the patient whose fluoroscopic image data is to be picked up and generates injection history data according to the injection; and
    a second computer that registers the injection history data in the first computer in association with the corresponding imaging order data,
    wherein the injection history data comprises a change of actual measured injection rate over time.

2. The fluoroscopic imaging system according to claim 1, wherein said second computer acquires said imaging order data corresponding to said injection history data from at least one of said first computer and said imaging diagnostic apparatus, and allocates at least a part of said imaging order data to said injection history data as identification data; and
    said first computer stores said injection history data in association with imaging order data via said identification data.

3. The fluoroscopic imaging system according to claim 2, wherein said first computer manages each of said imaging order data with exclusive identification data; and
    said second computer allocates said identification data of said imaging order data to said injection history data.

4. The fluoroscopic imaging system according to claim 3, wherein said imaging diagnostic apparatus allocates said identification data of said imaging order data to said fluoroscopic image data.

5. The fluoroscopic imaging system according to claim 3, wherein said imaging diagnostic apparatus and said second computer are connected to said first computer via a communication network;
    said first computer manages a plurality of said imaging order data;
    said imaging diagnostic apparatus transmits a response request for said imaging order data to said first computer;
    said first computer returns a plurality of said imaging order data according to said response request received from said imaging diagnostic apparatus; and
    said imaging diagnostic apparatus accepts an operation of selecting one of said plurality of imaging order data returned, and transfers said one selected from said imaging order data, to said second computer.

6. The fluoroscopic imaging system according to claim 2, wherein said imaging diagnostic apparatus and said second computer are connected to said first computer via a communication network;
    said first computer manages a plurality of said imaging order data, and accepts an operation of selecting one of said plurality of imaging order data being managed;
    said imaging diagnostic apparatus transmits a response request for said imaging order data to said first computer;
    said first computer returns one of said imaging order data selected according to said response request received from said imaging diagnostic apparatus;
    said second computer transmits said response request for said imaging order data to said first computer at a predetermined timing corresponding to said injection of said medical liquid; and
    said first computer returns said one of said imaging order data according to said response request received from said second computer.

7. The fluoroscopic imaging system according to claim 6, wherein said second computer transmits a response request for said imaging order data to said first computer with at least one order retrieval key;
    said first computer retrieves a part of said plurality of imaging order data according to said order retrieval key received from said second computer, and returns said one selected from said imaging order data if said part of said imaging order data includes said one selected.

8. The fluoroscopic imaging system according to claim 7, wherein said liquid injector transmits said generated injection history data to said second computer; and
    said second computer transmits at least a part of said injection history data received to said first computer as said order retrieval key.

9. The fluoroscopic imaging system according to claim 6, wherein said liquid injector notifies said second computer of at least one of start and finish of said injection of said medical liquid; and
    said second computer tranbsmits said response request according to said notice from said liquid injector.

10. The fluoroscopic imaging system according to claim 9, wherein said liquid injector is adapted to sequentially inject a contrast medium and physiological saline as said medical liquid into said patient, and notifies said second computer of at least finish of said injection of said contrast medium and start of said injection of said physiological saline.

11. The fluoroscopic imaging system according to claim 6, wherein said liquid injector notifies said second computer of at least one of start and finish of said injection of said medical liquid after a predetermined time; and
said second computer transmits said response request according to said notice from said liquid injector.

12. The fluoroscopic imaging system according to claim 6, wherein said liquid injector notifies said second computer of at least one of start and finish of said injection of said medical liquid; and
said second computer tranbsmits said response request, a predetermined time after said notice from said liquid injector.

13. The fluoroscopic imaging system according to claim 6, wherein said imaging diagnostic apparatus notifies said second computer of at least one of start and finish of said fluoroscopic image pickup; and
said second computer transmits said response request according to said notice from said imaging diagnostic apparatus.

14. The fluoroscopic imaging system according to claim 6, wherein said imaging diagnostic apparatus notifies said second computer of at least one of start and finish of said fluoroscopic image pickup after a predetermined time; and
said second computer transmits said response request according to said notice from said imaging diagnostic apparatus.

15. The fluoroscopic imaging system according to claim 6, wherein said imaging diagnostic apparatus notifies said second computer of at least one of start and finish of said fluoroscopic image pickup after a predetermined time; and
said second computer transmits said response request a predetermined time after said notice from said imaging diagnostic apparatus.

16. The fluoroscopic imaging system according to claim 2, wherein said imaging diagnostic apparatus and said second computer are connected to said first computer via a communication network;
said first computer manages a plurality of said imaging order data;
said imaging diagnostic apparatus transmits a response request for said imaging order data to said first computer with at least one order retrieval key;
said first computer selects and returns one of said plurality of imaging order data according to said response request received from said imaging diagnostic apparatus and said order retrieval key;
said second computer transmits said response request for said imaging order data to said first computer at a predetermined timing corresponding to said injection of said medical liquid; and
said first computer returns said one of said imaging order data according to said response request received from said second computer.

17. The fluoroscopic imaging system according to claim 2, wherein said imaging diagnostic apparatus and said second computer are connected to said first computer via a communication network;
said first computer manages a plurality of said imaging order data;
said imaging diagnostic apparatus transmits a response request for said imaging order data to said first computer;
said first computer returns a plurality of said imaging order data according to said response request received from said imaging diagnostic apparatus;
said imaging diagnostic apparatus accepts an operation of selecting one of said plurality of imaging order data returned, and notifies said first computer of said one selected from said imaging order data;
said second computer transmits said response request for said imaging order data to said first computer at a predetermined timing corresponding to said injection of said medical liquid; and
said first computer returns said one of said imaging order data notified of by said imaging diagnostic apparatus according to said response request received from said second computer.

18. The fluoroscopic imaging system according to claim 17, wherein said second computer transmits a response request for said imaging order data to said first computer with at least one order retrieval key;
said first computer retrieves a part of said plurality of imaging order data according to said order retrieval key received from said second computer, and returns said one of said imaging order data if said part of said imaging order data includes said one notified of by said imaging diagnostic apparatus.

19. The fluoroscopic imaging system according to claim 2, wherein said imaging diagnostic apparatus and said second computer are connected to said first computer via a communication network;
said first computer manages a plurality of said imaging order data;
said imaging diagnostic apparatus transmits a response request for said imaging order data to said first computer with at least one order retrieval key;
said first computer retrieves and returns a part of said plurality of imaging order data according to said response request received from said imaging diagnostic apparatus and said order retrieval key;
said imaging diagnostic apparatus accepts an operation of selecting one of said imaging order data returned, and notifies said first computer of said one selected from said imaging order data;
said second computer transmits said response request for said imaging order data to said first computer at a predetermined timing corresponding to said injection of said medical liquid; and
said first computer returns said one of said imaging order data notified of by said imaging diagnostic apparatus according to said response request received from said second computer.

20. The fluoroscopic imaging system according to claim 2, wherein said imaging diagnostic apparatus and said second computer are connected to said first computer via a communication network;
said first computer manages a plurality of said imaging order data, and accepts an operation of selecting one of said plurality of imaging order data being managed;
said imaging diagnostic apparatus transmits a response request for said imaging order data to said first computer;

said first computer returns one of said imaging order data selected according to said response request received from said imaging diagnostic apparatus;

said second computer transmits said response request for said imaging order data to said imaging diagnostic apparatus at a predetermined timing corresponding to said injection of said medical liquid; and said imaging diagnostic apparatus returns said imaging order data according to said response request received from said second computer.

21. The fluoroscopic imaging system according to claim 2, wherein said imaging diagnostic apparatus and said second computer are connected to said first computer via a communication network;

said first computer manages a plurality of said imaging order data;

said imaging diagnostic apparatus transmits a response request for said imaging order data to said first computer with at least one order retrieval key;

said first computer selects and returns one of said plurality of imaging order data according to said response request received from said imaging diagnostic apparatus and said order retrieval key;

said second computer transmits said response request for said imaging order data to said imaging diagnostic apparatus at a predetermined timing corresponding to said injection of said medical liquid; and said imaging diagnostic apparatus returns said imaging order data according to said response request received from said second computer.

22. The fluoroscopic imaging system according to claim 2, wherein said imaging diagnostic apparatus and said second computer are connected to said first computer via a communication network;

said first computer manages a plurality of said imaging order data;

said imaging diagnostic apparatus transmits a response request for said imaging order data to said first computer;

said first computer returns a plurality of said imaging order data according to said response request received from said imaging diagnostic apparatus;

said imaging diagnostic apparatus accepts an operation of selecting one of said plurality of imaging order data returned;

said second computer transmits said response request for said imaging order data to said imaging diagnostic apparatus at a predetermined timing corresponding to said injection of said medical liquid; and said imaging diagnostic apparatus returns said imaging order data according to said response request received from said second computer.

23. The fluoroscopic imaging system according to claim 2, wherein said imaging diagnostic apparatus and said second computer are connected to said first computer via a communication network;

said first computer manages a plurality of said imaging order data, and accepts an operation of selecting one of said plurality of imaging order data being managed;

said imaging diagnostic apparatus transmits a response request for said imaging order data to said first computer;

said first computer returns one of said imaging order data selected according to said response request received from said imaging diagnostic apparatus; and said imaging diagnostic apparatus transfers said imaging order data returned, to said second computer.

24. The fluoroscopic imaging system according to claim 2, wherein said imaging diagnostic apparatus and said second computer are connected to said first computer via a communication network;

said first computer manages a plurality of said imaging order data;

said imaging diagnostic apparatus transmits a response request for said imaging order data to said first computer with at least one order retrieval key;

said first computer selects and returns one of said plurality of imaging order data according to said response request received from said imaging diagnostic apparatus and said order retrieval key; and said imaging diagnostic apparatus transfers said imaging order data returned, to said second computer.

25. A second computer for use in said fluoroscopic imaging system according to claim 2, comprising:

means for acquiring said injection history data from said liquid injector;

means for acquiring at least a part of said imaging order data corresponding to said injection history data as said identification data, from at least one of said first computer and said imaging diagnostic apparatus;

means for allocating said identification data to said injection history data; and means for outputting said injection history data allocated with said identification data, to said first computer.

26. The fluoroscopic imaging system according to claim 1, wherein said imaging diagnostic apparatus and said second computer are connected to said first computer via a communication network;

said first computer manages a plurality of said imaging order data, and accepts an operation of selecting one of said plurality of imaging order data being managed;

said imaging diagnostic apparatus transmits a response request for said imaging order data to said first computer;

said first computer returns one of said imaging order data selected according to said response request received from said imaging diagnostic apparatus;

said second computer transmits said injection history data to said first computer at a predetermined timing corresponding to said injection of said medical liquid; and said first computer stores said injection history data received from said second computer in association with said one selected from said imaging order data.

27. The fluoroscopic imaging system according to claim 26, wherein said second computer transmits said injection history data to said first computer with at least one order retrieval key; and said first computer retrieves a part of said plurality of said imaging order data according to said order retrieval key received from said second computer, and stores, in the case where said part of said imaging order data thus retrieved includes said one selected, said imaging order data in association with said injection history data.

28. The fluoroscopic imaging system according to claim 27, wherein said liquid injector transmits said injection history data generated to said second computer; and said second computer transmits at least a part of said injection history data received to said first computer, as said order retrieval key.

29. The fluoroscopic imaging system according to claim 26, wherein said liquid injector transmits said injection history data to said second computer upon completion of said injection of said medical liquid; and said second computer transmits said injection history data to said first computer upon receipt of said injection history data.

30. The fluoroscopic imaging system according to claim 26, wherein said liquid injector transmits said injection history data to said second computer, a predetermined time after completion of said injection of said medical liquid; and said second computer transmits said injection history data to said first computer upon receipt of said injection history data.

31. The fluoroscopic imaging system according to claim 26, wherein said liquid injector transmits said injection history data to said second computer upon completion of said injection of said medical liquid; and said second computer transmits said injection history data a predetermined time after receipt of said injection history data.

32. The fluoroscopic imaging system according to claim 26, wherein said liquid injector is adapted to sequentially inject a contrast medium and physiological saline as said medical liquid into said patient, and transmits said injection history data of said second computer of at least finish of said injection of said contrast medium to said second computer, upon completion of said injection of said medical liquid.

33. The fluoroscopic imaging system according to claim 1, wherein said imaging diagnostic apparatus and said second computer are connected to said first computer via a communication network;

said first computer manages a plurality of said imaging order data;

said imaging diagnostic apparatus transmits a response request for said imaging order data to said first computer with at least one order retrieval key;

said first computer selects and returns one of said plurality of imaging order data according to said response request received from said imaging diagnostic apparatus and said order retrieval key;

said second computer transmits said injection history data to said first computer at a predetermined timing corresponding to said injection of said medical liquid; and said first computer stores said injection history data received from said second computer in association with said one selected from said imaging order data.

34. The fluoroscopic imaging system according to claim 1, wherein said imaging diagnostic apparatus and said second computer are connected to said first computer via a communication network;

said first computer manages a plurality of said imaging order data;

said imaging diagnostic apparatus transmits a response request for said imaging order data to said first computer;

said first computer returns a plurality of said imaging order data according to said response request received from said imaging diagnostic apparatus;

said imaging diagnostic apparatus accepts an operation of selecting one of said plurality of imaging order data returned, and notifies said first computer of said imaging order data selected;

said second computer transmits said injection history data to said first computer at a predetermined timing corresponding to said injection of said medical liquid; and said first computer stores said injection history data received from said second computer in association with said one of said imaging order data notified of by said imaging diagnostic apparatus.

35. The fluoroscopic imaging system according to claim 34, wherein said second computer transmits said injection history data to said first computer with at least one order retrieval key; and said first computer retrieves a part of said plurality of said imaging order data according to said order retrieval key received from said second computer, and stores, in the case where said part of said imaging order data thus retrieved includes said one notified of by said imaging diagnostic apparatus, said imaging order data in association with said injection history data.

36. The fluoroscopic imaging system according to claim 1, wherein said imaging diagnostic apparatus and said second computer are connected to said first computer via a communication network;

said first computer manages a plurality of said imaging order data;

said imaging diagnostic apparatus transmits a response request for said imaging order data to said first computer with at least one order retrieval key;

said first computer retrieves and returns one of said plurality of imaging order data according to said response request received from said imaging diagnostic apparatus and said order retrieval key;

said imaging diagnostic apparatus accepts an operation of selecting one of said imaging order data returned, and notifies said first computer of said imaging order data selected;

said second computer transmits said injection history data to said first computer at a predetermined timing corresponding to said injection of said medical liquid; and said first computer stores said injection history data received from said second computer in association with said one of said imaging order data notified of by said imaging diagnostic apparatus.

37. The fluoroscopic imaging system according to claim 1, wherein said liquid injector includes:

means for variably adjusting an injection rate of said medical liquid with the lapse of time;

means for generating injection history data including a time-based graph in which one of a horizontal axis and a vertical axis represents said lapse of time and the other represents said injection rate; and means for outputting said injection history data generated, to said second computer.

38. A liquid injector for use in said fluoroscopic imaging system according to claim 37, comprising:

means for variably adjusting an injection rate of said medical liquid with the lapse of time;

means for generating injection history data including a time-based graph in which one of a horizontal axis and a vertical axis represents said lapse of time and the other represents said injection rate; and means for outputting said injection history data generated, to said second computer.

39. A second computer for use in said fluoroscopic imaging system according to claim 1, comprising a function to register said injection history data in said first computer in association with said imaging order data.

40. A liquid injector for use in said fluoroscopic imaging system according to claim 1, comprising:
   means for generating injection history data according to said injection of said medical liquid; and
   means for outputting said injection history data generated, to said second computer.

41. The fluoroscopic imaging system according to claim 1, wherein the imaging order data and the injection history data are stored in a hard disc drive.

42. The fluoroscopic imaging system according to claim 1, wherein the liquid injector and the second computer are integrally constituted.

43. The fluoroscopic imaging system according to claim 1, wherein the liquid injector comprises a third computer.

44. The fluoroscopic imaging system according to claim 1, wherein the first computer and the imaging diagnostic apparatus are integrally constituted.

45. The fluoroscopic imaging system according to claim 1, wherein the liquid injector is connected to the Internet.

46. The fluoroscopic imaging system according to claim 1, wherein the second computer is connected to the Internet.

47. The fluoroscopic imaging system according to claim 1, wherein the injection history data further comprises at least one selected from the group consisting of an injection job identification of each injection job, date and time of start and finish of the injection, identification data of the liquid injector, identification data of the medical liquid, identification data of a region to be imaged, and a time-based graph in which one of a horizontal axis and a vertical axis represents a lapse of time and the other represents an injection rate.

* * * * *